US011027066B2

(12) United States Patent
Wilmot et al.

(10) Patent No.: US 11,027,066 B2
(45) Date of Patent: Jun. 8, 2021

(54) THREE-CHAMBERED AUTOINJECTOR

(71) Applicant: Meridian Medical Technologies, Inc., Columbia, MD (US)

(72) Inventors: John Glyndwr Wilmot, Mount Airy, MD (US); Robert Leavitt Hill, Columbia, MD (US)

(73) Assignee: Meridian Medical Technologies, Inc., Columbia, MD (US)

( * ) Notice: Subject to any disclaimer, the term of this patent is extended or adjusted under 35 U.S.C. 154(b) by 284 days.

(21) Appl. No.: 15/784,448

(22) Filed: Oct. 16, 2017

(65) Prior Publication Data
US 2018/0036481 A1    Feb. 8, 2018

Related U.S. Application Data

(63) Continuation of application No. 13/976,198, filed as application No. PCT/IB2011/055989 on Dec. 28, 2011, now abandoned.

(60) Provisional application No. 61/428,304, filed on Dec. 30, 2010.

(51) Int. Cl.
*A61M 5/19* (2006.01)
*A61M 5/20* (2006.01)

(52) U.S. Cl.
CPC ............ *A61M 5/19* (2013.01); *A61M 5/2066* (2013.01); *A61M 5/2033* (2013.01); *A61M 2005/206* (2013.01)

(58) Field of Classification Search
CPC .............. A61M 2005/206; A61M 5/19; A61M 5/2033; A61M 5/2066
See application file for complete search history.

(56) References Cited

U.S. PATENT DOCUMENTS 7,556,614 B2 * 7/2009 Griffiths .............. A61M 5/2066
604/191
2004/0097874 A1   5/2004 Griffiths et al.

FOREIGN PATENT DOCUMENTS

WO    WO2005/042067    5/2005

* cited by examiner

*Primary Examiner* — Deanna K Hall
(74) *Attorney, Agent, or Firm* — Jason G. Tebbutt

(57) ABSTRACT

The present invention relates to a three-chambered autoinjector as well as to the methods of administering medicaments to a human using the three-chambered autoinjector. In certain embodiments, the autoinjector includes a first medicament in liquid form, a second medicament preferably in solid form, and a liquid composition for diluting the second medicament, and utilizes a three-chambered design so as to administer the first medicament and a solution comprising the second medicament and the liquid composition at different injection depths into the body of a human. In an alternative embodiment an autoinjector is provided that delivers medicaments at the same injection depth.

16 Claims, 5 Drawing Sheets

THREE-CHAMBERED AUTOINJECTOR

BACKGROUND

Technical Field

The present invention relates to an autoinjector with three chambers as well as to methods of administering medicaments to a human using the three-chambered autoinjector.

Background

Autoinjectors have become quite popular and have experienced widespread use due to a variety of advantages autoinjectors have over typical manual syringe injectors. A number of autoinjectors are commercially available, including EpiPen® (King Pharmaceuticals Inc.), Anapen® (Lincoln Medical Ltd.), Rebiject® II (EMD Serono and Pfizer Inc.), and SureClick™ (Amgen). Generally speaking, an autoinjector is an automatic injection system that is designed to deliver a medicament into an individual upon activation of a power assembly. Among other things, autoinjectors generally comprise a housing, a medicament situated within the housing, a needle, and a power assembly. After activation of the power assembly, the needle moves from a storage position in which the needle is situated within the housing to an active position in which the needle extends from the housing and delivers the medicament to a patient.

There is a continuing need for improved autoinjector devices.

BRIEF SUMMARY

In one aspect, the present invention provides a three-chambered autoinjector. The autoinjector includes a housing having a forward end and a rear end. In certain embodiments, the autoinjector further includes an activatable power assembly, a rear plunger, a first chamber comprising a liquid composition, a separation assembly, a second chamber comprising a second medicament, a separation plunger, a third chamber comprising a first medicament, a needle, and a bypass within the housing.

The first medicament is in a liquid form and, preferably, the second medicament is in a solid form, which can be dissolved in the liquid composition. More preferably, the second medicament is in a lyophilized form.

In an alternative embodiment, both the first and the second medicaments are in liquid forms.

The rear plunger is moveably situated in the housing and is operatively linked to the power assembly so that after activation of the power assembly, the power assembly moves the rear plunger forwardly within the housing. The rear plunger rearwardly confines the first chamber.

The separation assembly is moveably situated in the housing and forwardly confines the first chamber and rearwardly confines the second chamber. The separation assembly comprises a separation assembly bypass having a closed position in which the separation assembly bypass prohibits the liquid composition from flowing through the separation assembly and an open position for allowing the liquid composition to flow through the separation assembly and into the second chamber. After activation of the power assembly, the separation assembly bypass moves from the closed position to the open position, allowing the liquid composition to enter the second chamber.

The separation plunger is moveably situated in the housing and forwardly confines the second chamber. After activation of the power assembly, the separation plunger moves forwardly within the housing.

The third chamber is rearwardly confined by the separation plunger and comprises a liquid medicament. In addition to the liquid medicament, the third chamber comprises a gas such as air, so that after activation of the power assembly, the gas in the third chamber can be compressed and allow the separation plunger to move forwardly within the housing.

The autoinjector further includes a needle having a needle length, a forward end and a rear end. Prior to the activation of the power assembly, the needle is in a needle storage position in which the needle is situated within the housing. After activation of the power assembly, the needle moves from the needle storage position to a needle fully extended position in which the needle reaches a maximal extension out of the forward end of the housing.

A bypass within the housing is forwardly situated with respect to the separation plunger prior to the activation of the power assembly and the bypass forms a bypass area within the housing for receiving the separation plunger. Prior to the separation plunger entering into the bypass area, the separation plunger creates a seal so as to prevent a solution comprising the liquid composition and the second medicament from flowing from the second chamber into the third chamber. When the separation plunger is received in the bypass area, the separation plunger no longer creates a seal between the second chamber and the third chamber and thus permits a solution comprising the liquid composition and the second medicament to flow around the separation plunger and into the needle.

The three-chambered design preferably enables all or substantially all of the liquid medicament to be delivered to a human as the needle moves from the needle storage position to the needle fully extended position and the design enables a solution comprising the liquid composition and the second medicament to be delivered after the needle reaches the needle fully extended position. As a result, in a preferred embodiment, the medicaments are delivered at different injection depths so as to prevent the medicaments from affecting the absorption of one another in the human's body.

Another advantage of the present invention is that it allows for the inclusion of more storage-stable forms (e.g., lyophilized forms) of medicaments that, when stored in liquid form, tend to become less pure, degrade and/or experience other unwanted effects.

Another advantage is that regulatory provisions in some jurisdictions may prohibit the storage of mixed cocktails of multiple medicaments, and the present invention provides for separate storage of the medicaments and the mixture of the medicaments immediately prior to injection.

In another embodiment of the invention, a moveable internal medicament housing has a needle assembly attached to the forward end thereof. Two separation assemblies are received in the internal medicament housing and separate it into three chambers.

DETAILED DESCRIPTION

Figure 1:
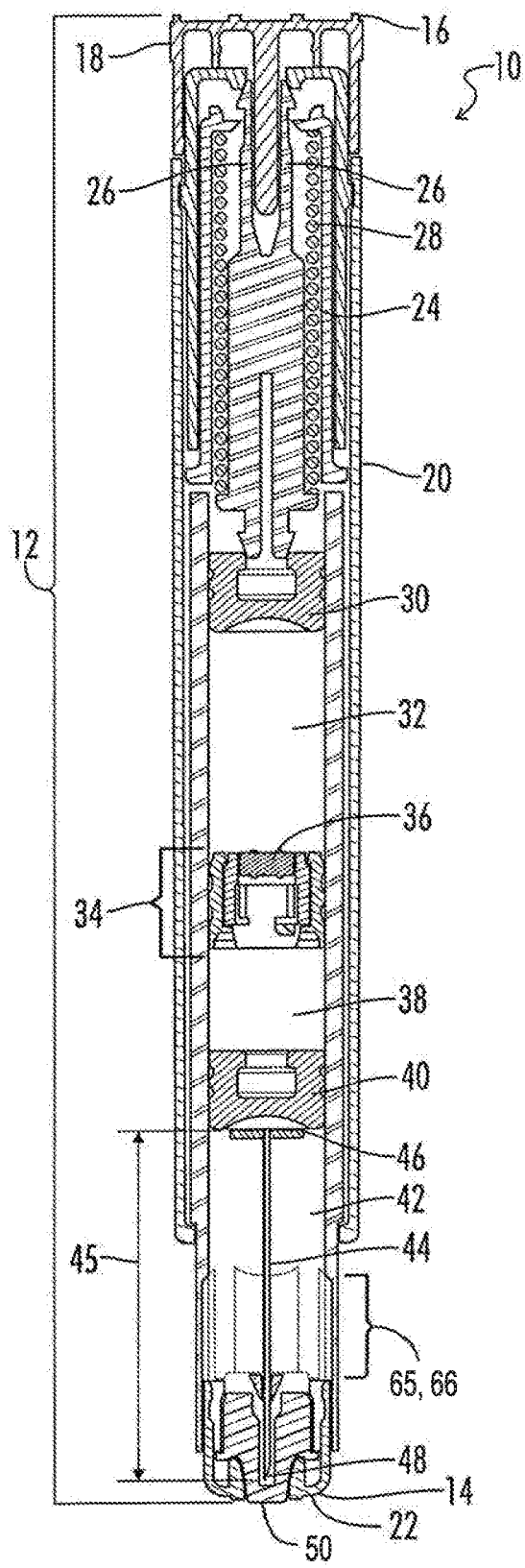
FIG. 1 illustrates a side cross-sectional view of an autoinjector in a loaded, activatable state.
Figure 2:
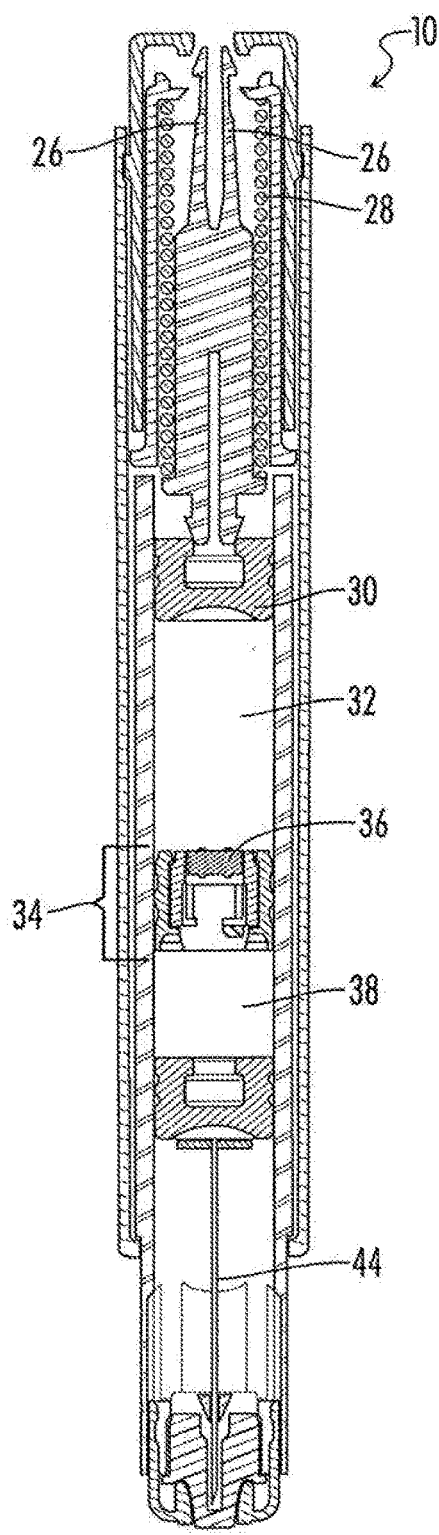
FIGS. 2-6 illustrate side cross-sectional views of an autoinjector after activation of the power assembly.
Figure 3:
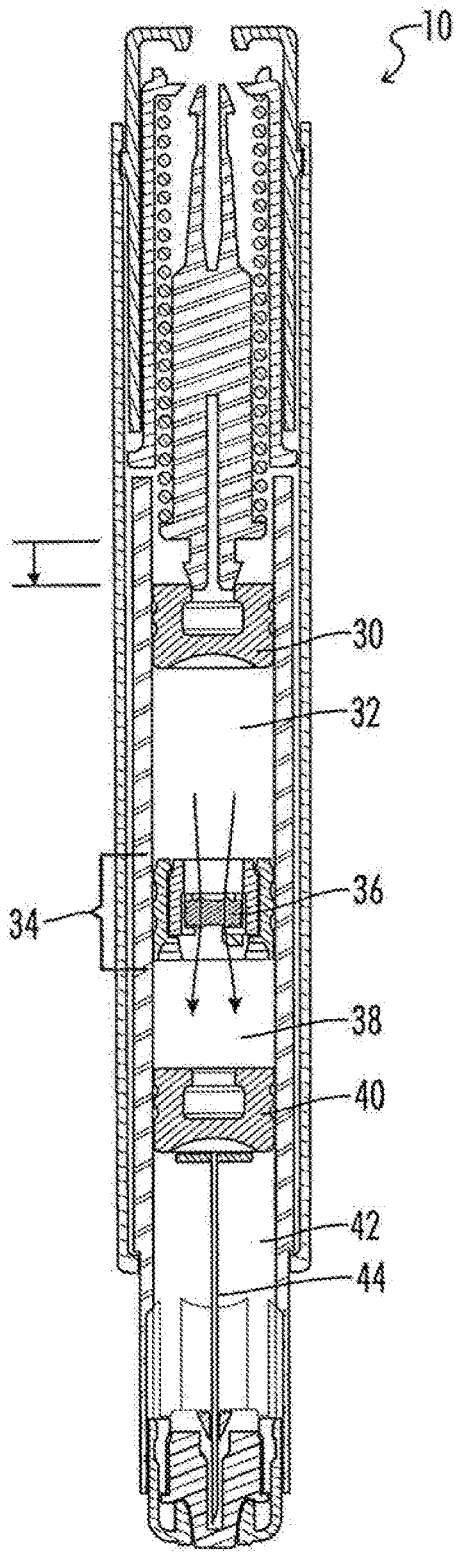
Figure 4:
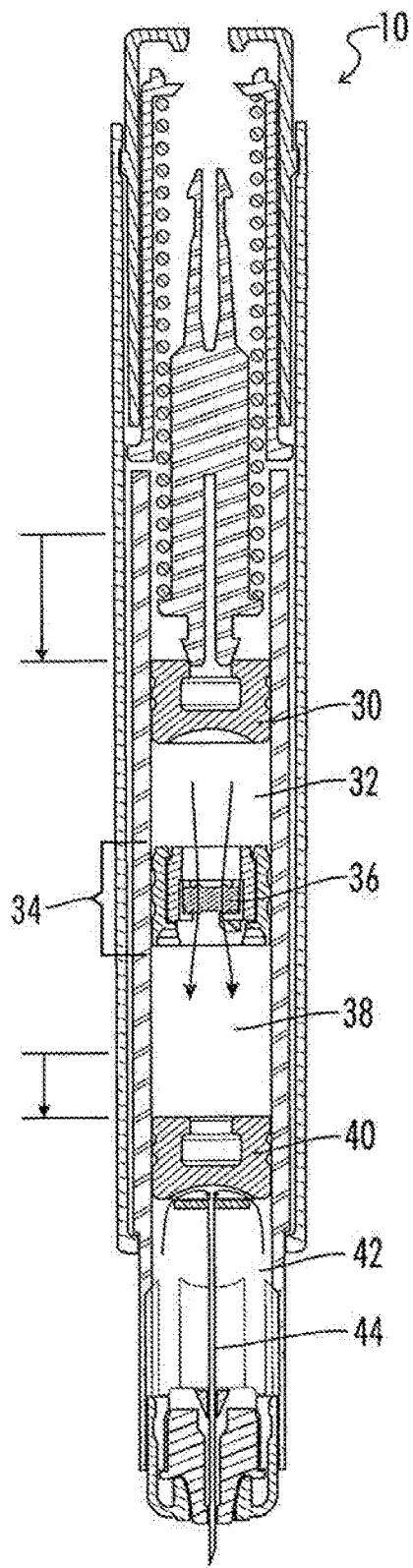
Figure 5:
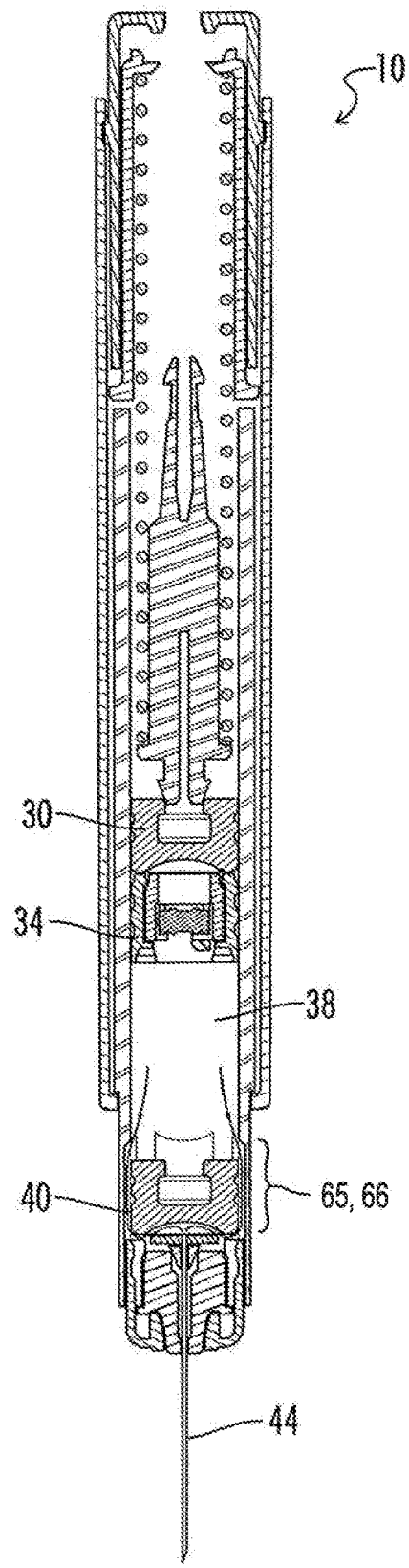
Figure 6:
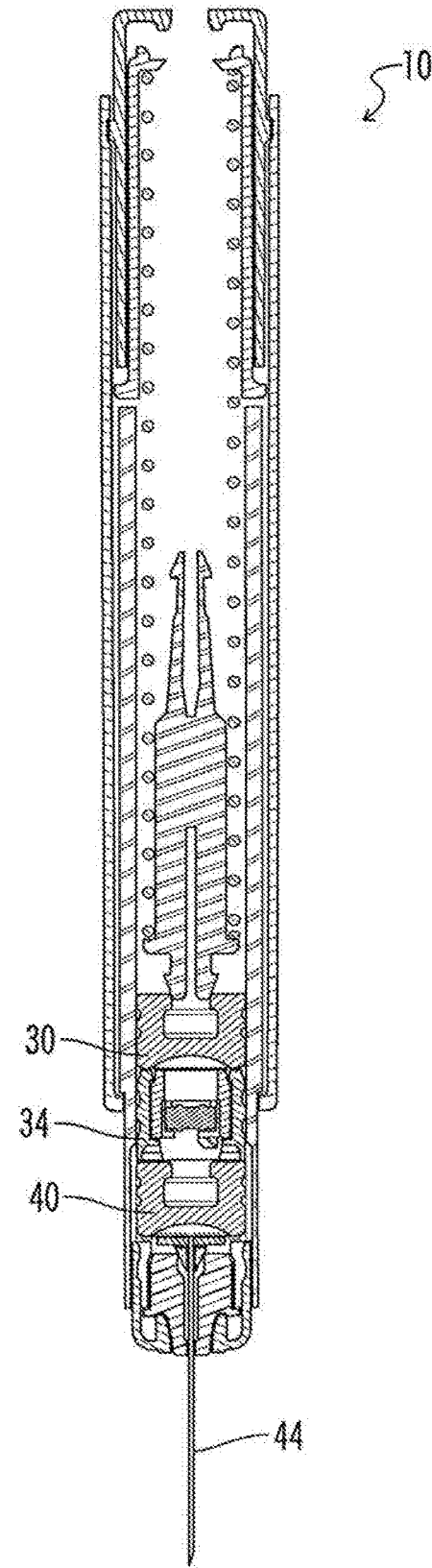

Referring now to the drawings, FIG. 1 illustrates a cross-sectional view of one embodiment of an autoinjector generally designated by the numeral 10. In the drawings, not all reference numbers are included in each drawing for the sake of clarity. In addition, positional terms such as "upper," "lower," "side," "top," "bottom," etc. refer to the apparatus when in the orientation shown in the drawing. The skilled artisan will recognize that the apparatus can assume different orientations when in use.

Referring further to FIG. 1, the autoinjector 10 comprises a housing 12 having a forward end 14 and a rear end 16. The housing 12 forms the exterior surface of the autoinjector body and can include one or more structures. For example, in FIG. 1, the housing 12 comprises a safety pin 18, a cylindrical body 20 and a needle cover 22. The housing 12, preferably, is generally hollow and can be comprised of any material. Preferably, the housing 12 is plastic, but it could also be formed from glass.

Situated within the housing 12 is an activatable power assembly 24. Power assemblies for autoinjector devices are well-known to those of ordinary skill and are described in, for example, U.S. Pat. No. 7,449,012, the contents of which is incorporated herein by reference in its entirety. Preferably, the power assembly 24 comprises deformable collet arms 26 and a spring 28. In certain embodiments, the power assembly 24 is activated by removing the safety pin 18 and positioning the autoinjector 10 on the body of a human. More particularly, in certain embodiments, the power assembly 24 is activated by removing the safety pin 18 and pressing the forward end 14 of the autoinjector housing 12 against a desired injection site on a human's body.

FIG. 1 shows the autoinjector in a loaded, activatable state—i.e., the power assembly 24 of the autoinjector 10 is capable of being activated, but has not been activated and the autoinjector 10 includes a first medicament in a liquid form, a second medicament, and a liquid composition so that the autoinjector 10 may deliver medicaments to a patient. The second medicament is preferably in a solid form and the liquid composition is for diluting the second (solid) medicament This preferred embodiment will be further described in the rest of the description.

However, it will be understood that the autoinjector 10 may include a first medicament in a liquid form and a second medicament also in a liquid form.

It will also be appreciated that other states of the autoinjector 10, for example, prior to loading with medicaments and the liquid composition or after activation of the power assembly 24, are also within the scope of the present invention. For example, FIGS. 2-6 illustrate the autoinjector 10 after activation of the power assembly 24.

Referring further to FIG. 1, the autoinjector 10 further includes a rear plunger 30 moveably situated within the housing 12. The rear plunger 30 is operatively linked to the power assembly 24 so that after activation of the power assembly 24, the power assembly 24 moves the rear plunger 30 forwardly within the housing 12.

The autoinjector 10 further includes a first chamber 32 comprising a liquid composition. The first chamber 32, and liquid composition contained therein, are rearwardly confined by the rear plunger 30. It is also noted that the position of the rear plunger 30 relative to the power assembly 24 may be adjusted to adjust the volume of the chamber 32.

The autoinjector 10 further includes a separation assembly 34, which is moveably situated in the housing 12 and forwardly confines the first chamber 32. The separation assembly 34 comprises a separation assembly bypass 36, which has a closed position in which the separation assembly bypass 36 prohibits a liquid composition contained in the first chamber 32 from flowing through the separation assembly 34 and an open position for allowing a liquid composition contained in the first chamber 32 to flow through the separation assembly 34 and forwardly within the housing 12. After activation of the power assembly 24, the separation assembly bypass 36 moves from the closed position to the open position, allowing the liquid composition to flow from the first chamber 32, through the separation assembly 34 and forwardly within the housing 12.

Separation assembly bypasses for autoinjector devices are described in, for example, U.S. Patent Publication No. 2004/0097874, the contents of which is incorporated by reference in its entirety.

The autoinjector 10 further includes a second chamber 38 comprising a solid medicament. The second chamber 38, and solid medicament contained therein, are rearwardly confined by the separation assembly 34. In certain embodiments, the solid medicament is in powder form. Preferably, the solid medicament is a lyophilized medicament—i.e., a medicament that has been subjected to lyophilization, otherwise known as freeze-drying. The solid medicament is referred to herein as "the second medicament", as it is the second medicament to be delivered from the autoinjector 10 to a patient.

The liquid composition included in the first chamber 32 and the second medicament included in the second chamber 38 are selected so that the second medicament is soluble in the liquid composition, because, upon opening of the separation assembly bypass 36, the liquid composition flows into the second chamber 38 and mixes with, and dissolves, the second medicament so as to create a solution comprising the second medicament and the liquid composition. Preferably, the liquid composition is an aqueous solution. In certain embodiments, the liquid composition included in the first chamber 32 comprises a medicament, thus, allowing the autoinjector 10 to deliver three medicaments to a patient.

In addition, in certain alternative embodiments, instead of a medicament in solid form, the second chamber 38 can comprise a liquid medicament. In such embodiments, upon opening of the separation assembly bypass 36, the liquid composition flows into the second chamber 38 and mixes with the liquid medicament in the second chamber 38 so as to form a solution comprising the liquid medicament and the liquid composition.

The autoinjector 10 further includes a separation plunger 40, which is moveably situated within the housing and forwardly confines the second chamber 38. After activation of the power assembly 24 and after the liquid composition begins to move through the separation assembly 34 and into the second chamber 38, the separation plunger 40 moves forwardly within the housing 10.

The autoinjector 10 further includes a third chamber 42 comprising a liquid medicament. The third chamber 42, and liquid medicament contained therein, are rearwardly confined by the separation plunger 40. The liquid medicament is referred to herein as "the first medicament", as it is the first medicament to be delivered from the autoinjector 10 to a patient. In addition to the first medicament, the third chamber 42 comprises a gas which may be air but is preferably an inert gas, so that after activation of the power assembly 24, the gas in the third chamber 42 can be compressed and allow the separation plunger 40 to move forwardly within the housing 12.

The autoinjector 10 further includes a needle 44 having a needle length 45, a forward end 48 and a rear end 46. As shown, in FIG. 1, the needle 44 is in a needle storage position in which the needle 44 is situated within the housing 12. After activation of the power assembly 24, the needle 44 moves from the needle storage position to a needle fully extended position in which the needle 44 reaches a maximal extension out of the forward end of the housing 12.

As shown in FIG. 1, preferably, the needle cover 22 comprises a punctureable sheath 50 situated over the forward end 48 of the needle 44 so that the needle 44 can puncture through the sheath 50 and extend from the housing 12 after activation of the power assembly 24. It is also possible in some embodiments of a triple chamber autoinjector to have a needle sheath that would be manually removed prior to use.

Figure 7:
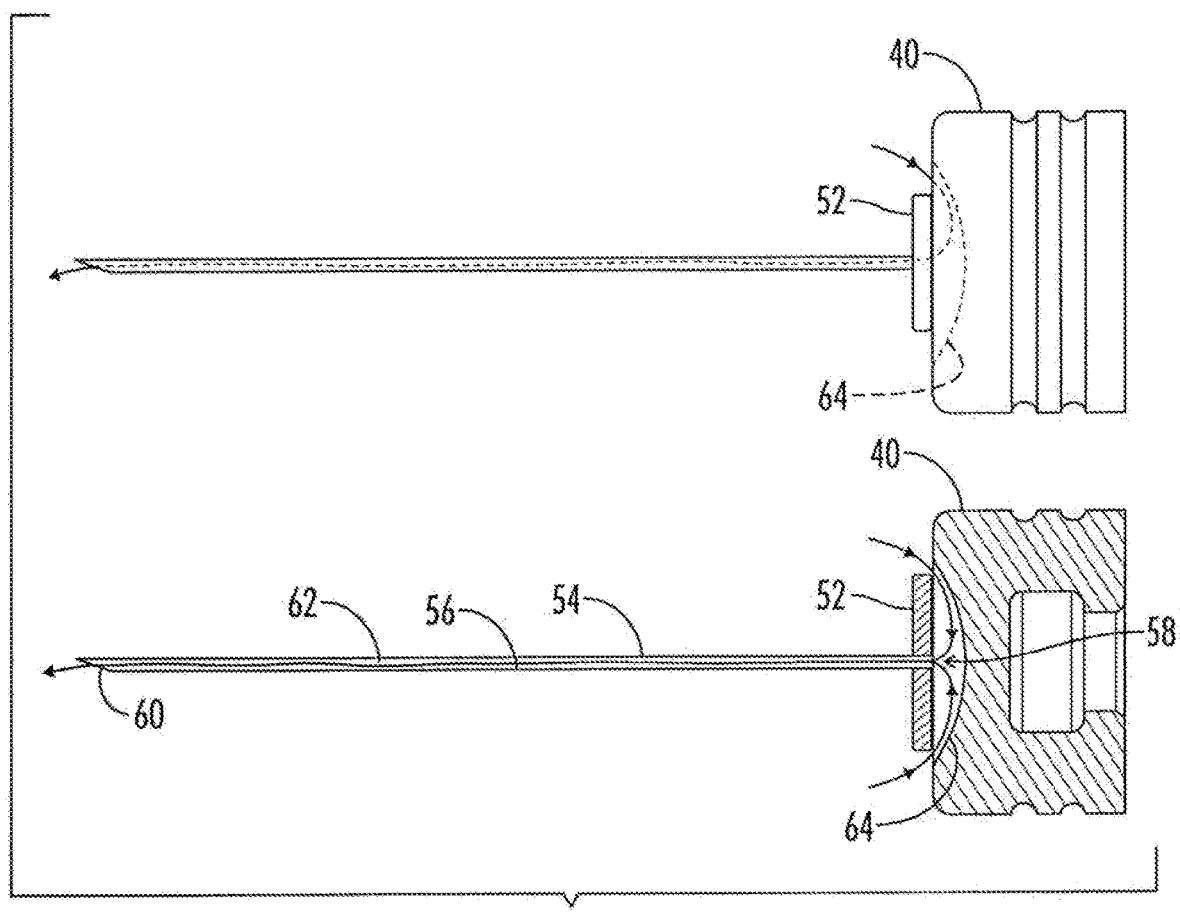
FIG. 7 illustrates a side schematic view and a side cross-sectional view of an autoinjector needle resting on a concave surface of the separation plunger and further illustrates the flow of a medicament through the needle.
Figure 8:
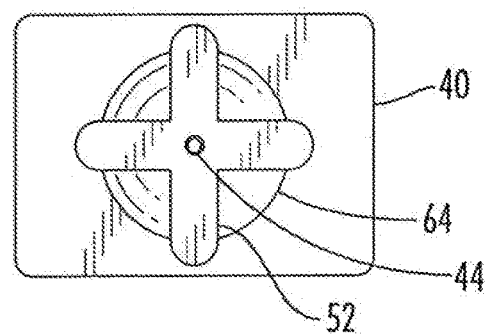
FIG. 8 illustrates a top schematic view of an autoinjector needle and separation plunger.

An illustrative needle for use in the present invention is shown in FIGS. 7 and 8. As shown, the needle 44 comprises a needle base 52, an interior 54, an exterior 56, a first opening 58 for allowing the first medicament and a solution comprising the second medicament and the liquid composition to enter into the interior 54 of the needle 44 from the housing 12, a second opening 60 for allowing the first medicament and the solution to be ejected from the needle 44, and a passage 62 for allowing the first medicament and the solution to flow through the interior 54 of the needle 44 by entering through the first opening 58 and exiting from the second opening 60. The needle base 52 preferably rests on, but does not cover, a concave surface 64 of the separation plunger 40, which allows the first medicament and the solution to flow into an area between the needle base 52 and the concave surface 64 of the separation plunger 40, enter into the first opening 58 in the needle 44, through the needle passage 62, and exit from the second opening 60 in the needle 44. In this embodiment, the first opening 58 of the needle 44 is located in the needle base 52.

However, it will be understood that other embodiments can be used in the present invention. For example, the first opening 58 of the needle 44 can be forwardly situated with respect to the base 52 and can comprise multiple slits located around the needle 44.

The autoinjector 10 further includes a bypass 65 within the housing 12. The bypass 65 is forwardly situated with respect to the separation plunger 40 prior to the activation of the power assembly 24 and the bypass 65 forms a bypass area 66 within the housing 12 for receiving the separation plunger 40. The bypass 65 may be in the form of grooves defined in the housing wall, an enlarged internal diameter of the housing wall, ribs extending inward from the housing wall, a cage-like insert received in the housing, or any combination of such structures adequate to permit fluid to flow around the separation plunger 40 when the separation plunger 40 is received in the bypass area 66. Prior to the separation plunger 40 entering into the bypass area 66, the separation plunger 40 creates a seal so as to prevent a solution comprising the liquid composition and the second medicament from flowing from the second chamber 38 into the third chamber 42. When the separation plunger is received in the bypass area 66, the separation plunger 40 no longer creates a seal between the second chamber 38 and the third chamber 42, thus, permitting a solution comprising the liquid composition and the second medicament to flow around the separation plunger 40 and into the first opening 58 in the needle 44.

An exemplary mode of operation and method of use is described below for an autoinjector loaded with the first medicament, the second medicament, and the liquid composition. It will be understood that the method of operation and method of use is only exemplary.

An autoinjector 10 is provided. The autoinjector is in its loaded, activatable state. See FIG. 1.

The safety pin 18 is removed and the forward end 14 of the autoinjector housing 12 is pressed against a desired injection site on the body of a human. The deformable collet arms 26 collapse to release energy from the spring 28. See FIG. 2. It is noted that the autoinjector may also be constructed to be activated by a push-button rather than by pressing of the autoinjector against the injection site.

The spring energy causes the rear plunger 30 to begin moving forwardly within the housing 12. The forwardly movement of the rear plunger 30 decreases the volume of and pressurizes the first chamber 32. The pressure built up within the first chamber 32 causes the separation assembly bypass 36 to move to the open position and the liquid composition to flow through the separation assembly 34 and into the second chamber 38. See FIG. 3.

The liquid composition begins to dissolve the second medicament to form a solution comprising the liquid composition and the second medicament. The liquid composition applies pressure on the separation plunger 40, causing the separation plunger 40 to move forwardly within the housing 12. The forwardly movement of the separation plunger 40, in turn, decreases the volume of, and compresses gas in, the third chamber 42 and causes the needle 44 to begin moving from the needle storage position to the needle fully extended position. As the needle 44 moves from the needle storage position to the needle fully extended position, the first medicament enters into the first opening 58 in the needle, flows through the passage 62 in the needle 44 and is ejected from the second opening 60 in the needle 44 and into the body of a human. The rear plunger 30 continues moving forwardly and aids the dissolution of the second medicament in the liquid composition. See FIG. 4; FIG. 7 (illustrating flow of a medicament through the needle).

The separation plunger 40 is received in the bypass area 66 and ceases moving forwardly within the housing 12. The needle 44 reaches the needle fully extended position and the first medicament ceases flowing through the passage 62 in the needle 44. A solution comprising the liquid composition and the second medicament flows from the second chamber 38, around the separation plunger 40, into the third chamber 42, and through the passage 62 in the needle 44. As the second medicament flows through the passage 62 in the needle 44, the rear plunger 30 and separation assembly 34 move forwardly within the housing 12. The forwardly movement of the separation assembly 34 decreases the volume of the second chamber 38. See FIG. 5; FIG. 7 (illustrating flow of a medicament through the needle).

The rear plunger 30 and the separation assembly 34 cease moving forwardly and the solution comprising the liquid composition and the second medicament ceases ejecting from the needle 44. The delivery of the medicaments is complete. Preferably, when the delivery of the medicaments is complete, the volumes of the first chamber 32, the second chamber 38, and the third chamber 42 have approached zero, which ensures that little to no medicaments remain in the autoinjector 10 when the delivery of the medicaments is complete. See FIG. 6.

As mentioned, the design of the autoinjector 10 allows the autoinjector 10 to administer the first medicament and a solution comprising the second medicament and the liquid composition at different injection depths into the body of a human. More particularly, due to the seal created by the separation plunger 40 prior to entering the bypass area 66, the autoinjector 10 delivers the first medicament as the needle 44 moves from the needle storage position to the needle fully extended position. The autoinjector 10 delivers a solution comprising the second medicament and the liquid composition after the needle 44 moves to the fully extended position. It will be appreciated that a small amount of the first medicament may be ejected from the needle 44 after the needle 44 moves to the needle fully extended position, as the solution comprising the second medicament and the liquid composition may wash residual amounts of the first medicament through the needle 44. However, preferably substantially all of the first medicament is delivered before the needle 44 reaches the needle fully extended position.

Figure 9:
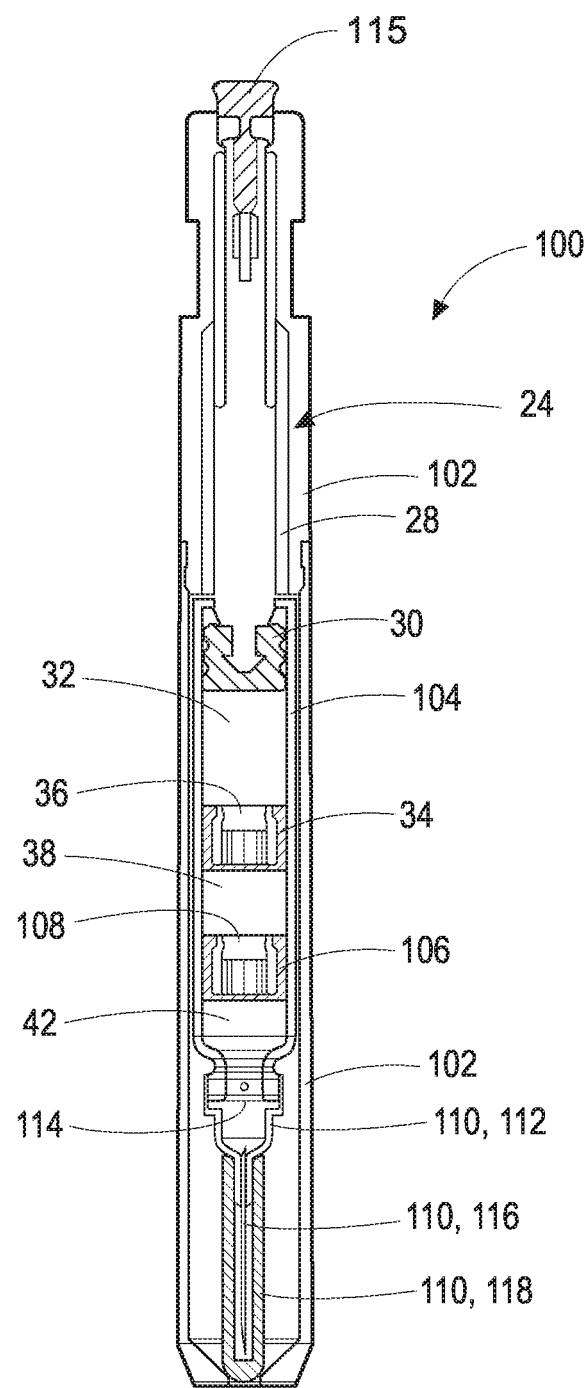
FIG. 9 is a side cross-sectional view of an alternative embodiment having a moveable internal medicament housing with two separation assemblies received in the internal medicament housing.

The Embodiment of FIG. 9

In FIG. 9 an alternative embodiment of the autoinjector is generally indicated by the numeral 100. In FIG. 9 parts identical to or analogous to those of the autoinjector 10 of FIG. 1 are labeled with like numerals.

The autoinjector 100 includes an external housing assembly 102 and a moveable internal medicament housing 104. The rear plunger 30 and the first separation assembly 34 are received in the bore of the internal medicament housing 104. Also received in the internal medicament housing 104 in place of the separation plunger 40 is a second separation assembly 106, which includes a bypass 108. A needle assembly 110 includes a needle hub 112 attached to the forward end of moveable internal medicament housing 104 for movement therewith relative to the external housing 102. The needle assembly 110 further includes a needle 116 and a collapsible needle sheath 118.

The chambers 32, 38 and 42 may contain medicaments and/or liquid compositions as previously described. A forward end of the third chamber 42 is preferably sealed by a burstable membrane 114.

In operation the autoinjector 100 functions generally as follows. The forward end of the external housing 104 is placed against a desired injection site on the body of the human. A push button actuator 115 is then pressed to release the spring 28.

The spring energy causes the rear plunger 30 to begin moving forwardly within the internal medicament housing 104. The bypass 36 of the first separation assembly 34 opens and the liquid composition flows from first chamber 32 through first separation assembly 34 into second chamber 38 and begins to dissolve the second medicament. Once second chamber 38 fills with liquid composition the hydraulic pressure applied on second separation assembly 106 will open second bypass 108 and will begin moving the entire internal medicament housing 104 and needle assembly 110 forward.

The sheath 118 will collapse and the needle 116 will pierce the end of the collapsible needle sheath 118 and will extend from the external housing 102 to its full insertion depth into the human. The medicament from the third chamber 42 and the dissolved medicament from second chamber 38 will flow substantially sequentially through the needle 116 into the human at the full needle insertion depth.

Having now described the invention in accordance with the requirements of the patent statutes, those skilled in the art will understand how to make changes and modifications to the disclosed embodiments to meet their specific requirements or conditions. Changes and modifications may be made without departing from the scope and spirit of the invention, as defined and limited solely by the following claims.

The invention claimed is:

1. An autoinjector comprising:
   a) a housing having a forward end and a rear end;
   b) a rear plunger moveably situated within the housing;
   c) a separation assembly moveably situated within the housing, the separation assembly forwardly situated with respect to the rear plunger;
   d) a separation plunger moveably situated within the housing, the separation plunger forwardly situated with respect to the separation assembly;
   e) a first medicament situated forwardly with respect to the separation plunger, the first medicament in the form of a liquid;
   f) a second medicament situated between the separation plunger and the separation assembly;
   g) a liquid composition situated between the separation assembly and the rear plunger;
   h) a needle having a needle length, a forward end and a rear end, the needle being moveable from a needle storage position in which the needle is situated within the housing to a needle fully extended position in which the needle reaches a maximal extension out of the forward end of the housing; and
   i) an activatable power assembly for moving the rear plunger forwardly within the housing.

2. The autoinjector of claim 1, wherein, after activation of the power assembly, the power assembly causes the separation plunger, the separation assembly, and the rear plunger to move forwardly within the housing and the needle to move from the needle storage position to the needle fully extended position.

3. The autoinjector of claim 1, wherein the separation assembly comprises a separation assembly bypass, the separation assembly bypass having a closed position in which the separation assembly bypass prohibits the liquid composition from flowing through the separation assembly and mixing with the second medicament and an open position for allowing the liquid composition to flow through the separation assembly and mix with the second medicament.

4. The autoinjector of claim 1, wherein the housing comprises a punctureable sheath situated over the forward end of the needle so that the needle can puncture through the sheath and extend from the housing after activation of the power assembly.

5. The autoinjector of claim 1, wherein the needle comprises an interior, an exterior, a first opening for allowing the first medicament and a solution comprising the liquid composition and the second medicament to enter into the interior of the needle from the housing, a second opening for allowing the first medicament and the solution to be ejected from the needle, and a passage for allowing the first medicament and the solution to flow through the interior of the needle by entering through the first opening and exiting from the second opening.

6. The autoinjector of claim 1, wherein the autoinjector further comprises a bypass within the housing, the bypass forwardly situated with respect to the separation plunger prior to the activation of the power assembly, the bypass forming a bypass area within the housing for receiving the separation plunger so that when the separation plunger is received in the bypass area, a solution comprising the liquid composition and the second medicament can flow around the separation plunger and into an opening in the needle.

7. The autoinjector of claim 1, wherein the separation plunger rearwardly confines the first medicament.

8. The autoinjector of claim 1, wherein the second medicament is in the form of a solid.

9. The autoinjector of claim 8, wherein the second medicament is a lyophilized medicament.

10. The autoinjector of claim 1, wherein the liquid composition is an aqueous solution.

11. An autoinjector having three chambers, the autoinjector comprising:
 a) a housing having a forward end and a rear end;
 b) a rear plunger moveably situated within the housing;
 c) a separation assembly moveably situated within the housing, the separation assembly forwardly situated with respect to the rear plunger;
 d) a separation plunger moveably situated within the housing, the separation plunger forwardly situated with respect to the separation assembly;
 e) a first chamber for a liquid composition, the first chamber having a variable volume, the first chamber forwardly confined by the separation assembly and rearwardly confined by the rear plunger;
 f) a second chamber for a second medicament, the second chamber having a variable volume, the second chamber forwardly confined by the separation plunger and rearwardly confined by the separation assembly;
 g) a third chamber for a first medicament, the third chamber having a variable volume, the third chamber rearwardly confined by the separation plunger;
 h) a needle having a needle length, a forward end and a rear end, the needle being moveable from a needle storage position in which the needle is situated within the housing to a needle fully extended position in which the needle reaches a maximal extension out of the forward end of the housing; and
 i) an activatable power assembly for moving the rear plunger forwardly within the housing.

12. The autoinjector according to claim 11, wherein, after activation of the power assembly, the power assembly causes i) the rear plunger to move forwardly within the housing so as to decrease the volume of the first chamber; ii) the separation assembly to move forwardly within the housing so as to decrease the volume of the second chamber; iii) the separation plunger to move forwardly within the housing so as to decrease the volume of the third chamber; and iv) the needle to move from the needle storage position to the needle fully extended position.

13. The autoinjector claim 11, wherein the separation assembly comprises a separation assembly bypass for allowing the liquid composition to flow from the first chamber through the separation assembly and into the second chamber.

14. The autoinjector of claim 11, including a first medicament contained in the third chamber, the first medicament in the form of a liquid.

15. The autoinjector of claim 11, including a second medicament contained in the second chamber, the second medicament in the form of a solid.

16. The autoinjector of claim 11, including a liquid composition contained in the first chamber.

* * * * *